United States Patent
Siess

(10) Patent No.: US 7,070,555 B2
(45) Date of Patent: Jul. 4, 2006

(54) INTRACARDIAC BLOOD PUMP

(75) Inventor: Thorsten Siess, Wuerselen (DE)

(73) Assignee: Impella CardioSystems AG (DE)

( * ) Notice: Subject to any disclaimer, the term of this patent is extended or adjusted under 35 U.S.C. 154(b) by 543 days.

(21) Appl. No.: 10/362,009

(22) PCT Filed: Jul. 10, 2001

(86) PCT No.: PCT/EP01/07953

§ 371 (c)(1),
(2), (4) Date: Feb. 18, 2003

(87) PCT Pub. No.: WO02/15963

PCT Pub. Date: Feb. 28, 2002

(65) Prior Publication Data

US 2003/0187322 A1    Oct. 2, 2003

(30) Foreign Application Priority Data

Aug. 18, 2000  (DE) .............................. 100 40 403

(51) Int. Cl.
*A61N 1/362*    (2006.01)
(52) U.S. Cl. .......................................... 600/16; 623/3.1
(58) Field of Classification Search ............ 600/16–18; 604/121, 151; 623/3.1, 3.13; 128/898
See application file for complete search history.

(56) References Cited

U.S. PATENT DOCUMENTS

| 5,275,580 | A | | 1/1994 | Yamazaki |
| 5,964,694 | A | | 10/1999 | Siess et al. |
| 6,058,593 | A | * | 5/2000 | Siess ............................ 29/596 |
| 6,139,487 | A | * | 10/2000 | Siess ............................ 600/16 |
| 6,176,822 | B1 | * | 1/2001 | Nix et al. ..................... 600/17 |
| 6,176,848 | B1 | * | 1/2001 | Rau et al. .................... 604/264 |
| 6,508,787 | B1 | * | 1/2003 | Erbel et al. ................. 604/151 |
| 6,544,216 | B1 | * | 4/2003 | Sammler et al. ......... 604/95.03 |

FOREIGN PATENT DOCUMENTS

| EP | 0764448 | 3/1997 |
| WO | WO 94/09835 | 5/1994 |

* cited by examiner

*Primary Examiner*—Robert E. Pezzuto
*Assistant Examiner*—Brian T. Gedeon
(74) *Attorney, Agent, or Firm*—Fulwider Patton LP

(57) ABSTRACT

The blood pump (10) comprises an elongate drive portion (11) and a pump portion (12) lengthening the latter. Between the two portions, flow openings (17) are positioned. According to the invention, the flow openings (17) are covered by a screen (24) preventing the blood pump from sucking fast on tissue parts or cardiac valves or from sucking in endogenous tissue and being blocked thereby.

12 Claims, 4 Drawing Sheets

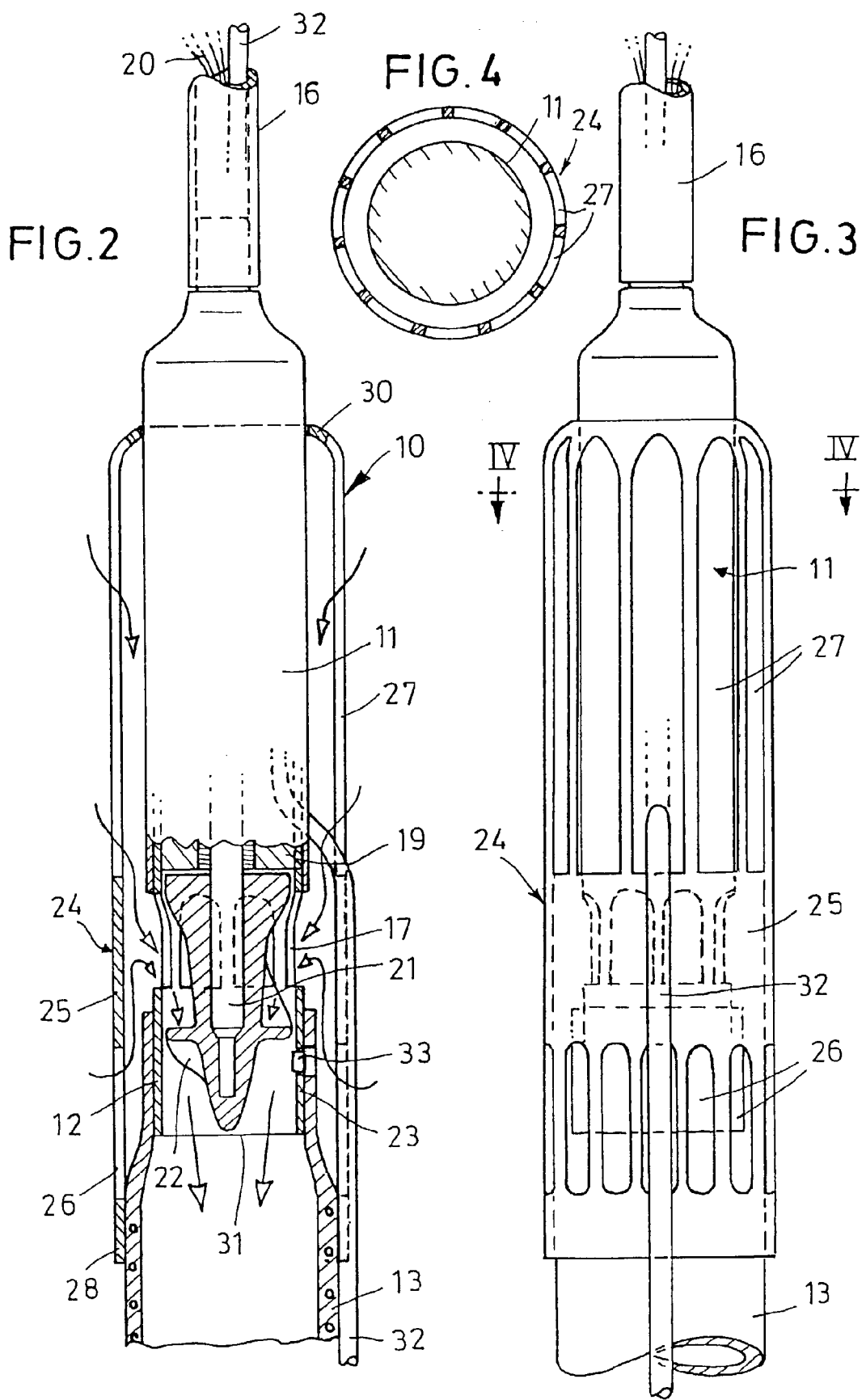

INTRACARDIAC BLOOD PUMP

Figure 1:
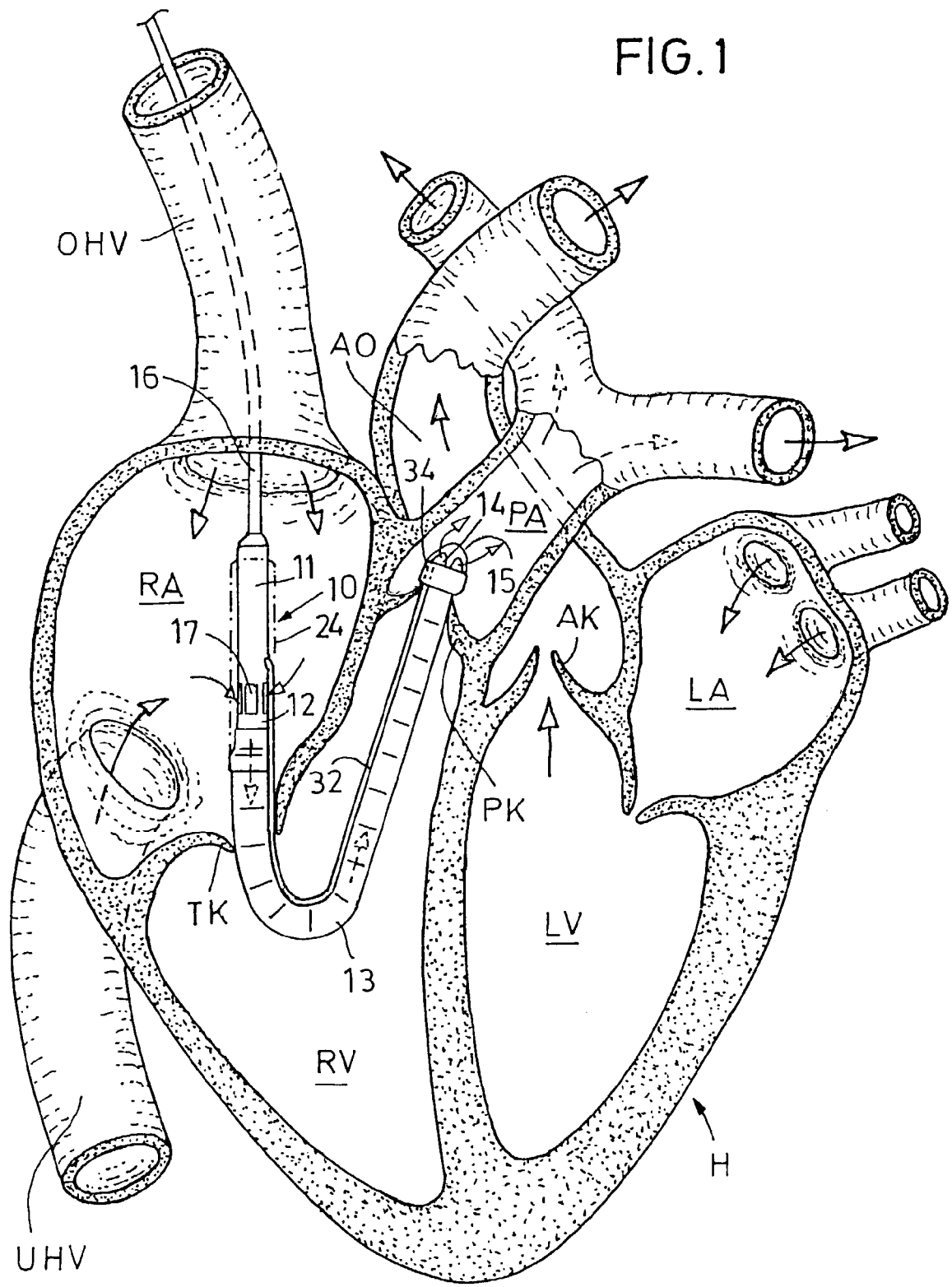

The invention relates to an intracardiac blood pump with a drive portion including a motor and a pump portion including a pump wheel driven by the motor, at least one lateral flow opening being provided between the drive portion and the pump portion.

An intracardiac blood pump is a blood pump that is at least partially introduced into the heart to deliver blood from the heart into an artery, wherein the pump protrudes through a surgical opening of the heart. Such intracardiac blood pumps have a maximum outer diameter of about 10–15 mm. A special form of intracardiac blood pumps are intravascular blood pumps. They are introduced into the heart through the vascular system of the patient, the incision site being spaced from the heart. Intravascular blood pumps have a diameter of about 8 mm at maximum and a rigid length of 35 mm at maximum.

Intravascular blood pumps are known from WO 94/09835 (Jarvik) and EP 0 764 448 A2 (Jarvik). An intravascular blood pump with an outer diameter of not more than about 6 mm is described in WO 97/37696.

DE 198 21 307 C1 describes the right ventricule operation of an intravascular blood pump. Here, the blood pump is positioned in the right atrium through the superior vena cava, and a flexible cannula connected to the pump outlet extends through the tricuspid valve into the right ventricle and from there through the pulmonary valve into the pulmonary artery. The pump delivers from the right atrium into the pulmonary artery leading to the lungs.

For an intravascular blood pump, a capacity of about 4.5 l/min at physiological pressures (60–80 mm Hg) is required. This high capacity leads to high flow velocities in the lateral inlet opening between drive portion and pump portion, resulting in that the blood pump generates a strong suction. Thereby, the blood pump may suck fast on the relatively thin wall of the right atrium. On the one hand, such a sucking-fast results in that the admission opening is partially closed and the required blood flow cannot be achieved, and, on the other hand, there is the danger of hurting the wall of the atrium. Furthermore, it may happen that tissue parts of the valvular apparatus are sucked into the pump and hydraulically obstruct or mechanically block it. The loss of function of a pump serving to support the heart may have critical consequences.

It is the object of the present invention to provide an intracardiac blood pump permitting a trouble-free continuous operation without the danger of sucking fast or sucking in body matter.

This object is solved, according to the invention, with the features indicated in claim 1. Accordingly, the flow opening provided between drive portion and pump portion is covered by a screen diverting the blood stream passing the flow opening. The blood stream passes the flow opening in radial direction with respect to the longitudinal axis of the blood pump, this blood stream, however, does not effect any radial pressure or suction. The screen rather diverts the pressure or suction into an axial direction with respect to the longitudinal axis of the blood pump.

Depending on the rotational direction of the motor and shape of the pump wheel, the blood pump can be operated with different delivery directions. In one case, the flow opening between drive portion and pump portion is an admission opening, and in the other case, it is a discharge opening. In both cases, the screen that is arranged at a distance above the passage opening has an advantageous effect on the operational behavior. When the flow opening acts as an admission opening, the screen prevents the pump of sucking fast on external parts in that the inlet opening is enlarged and spatially distributed. When the blood pump is operated such that the flow opening forms the discharge opening, the screen effects an effective shortening of the structural length of the blood pump, as will be explained later on. This permits to position the pump in the pulmonary artery without running any risk of shunt flows through the pulmonary valve.

Another aspect of the invention consists in that the pump portion may be provided with a pressure sensor that measures the pressure outside and or inside the pump portion and determines the capacity of the pump on the basis of the measured value and further detects and signals extraordinary operational conditions such as, e.g., a locking of the line. Such a sensor is covered over by the screen so that there is no danger that the sensor is pressed against a wall under the influence of the flow effects and therefore supplies wrong pressure values. The sensor, which is exposed under the screen, cannot be separated from the suction region and the actual suction pressure. When a suction is effected, this will be detected by the sensor.

Hereinafter, embodiments of the invention are explained in detail with reference to the drawings.

Figure 5:
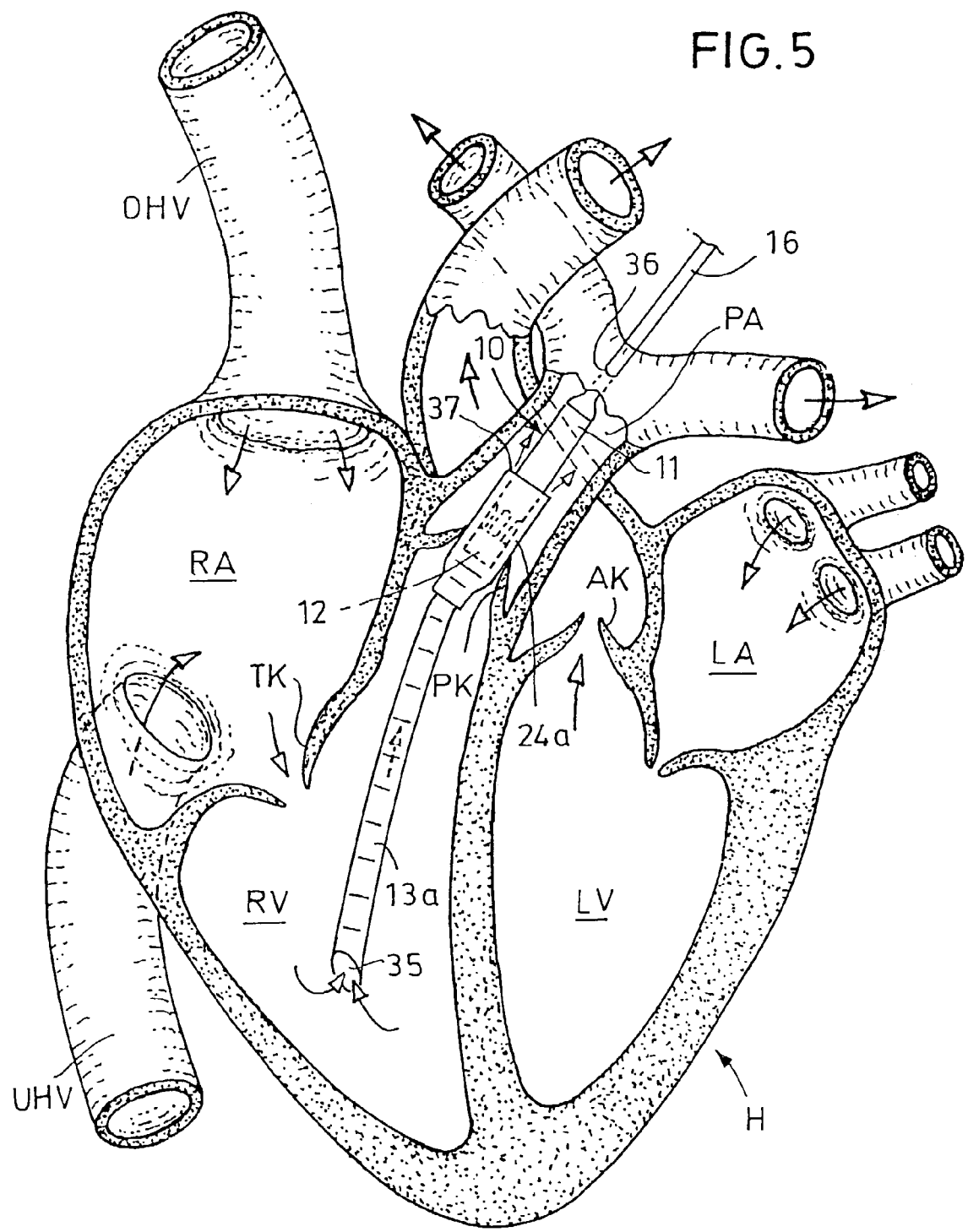
Figure 6:
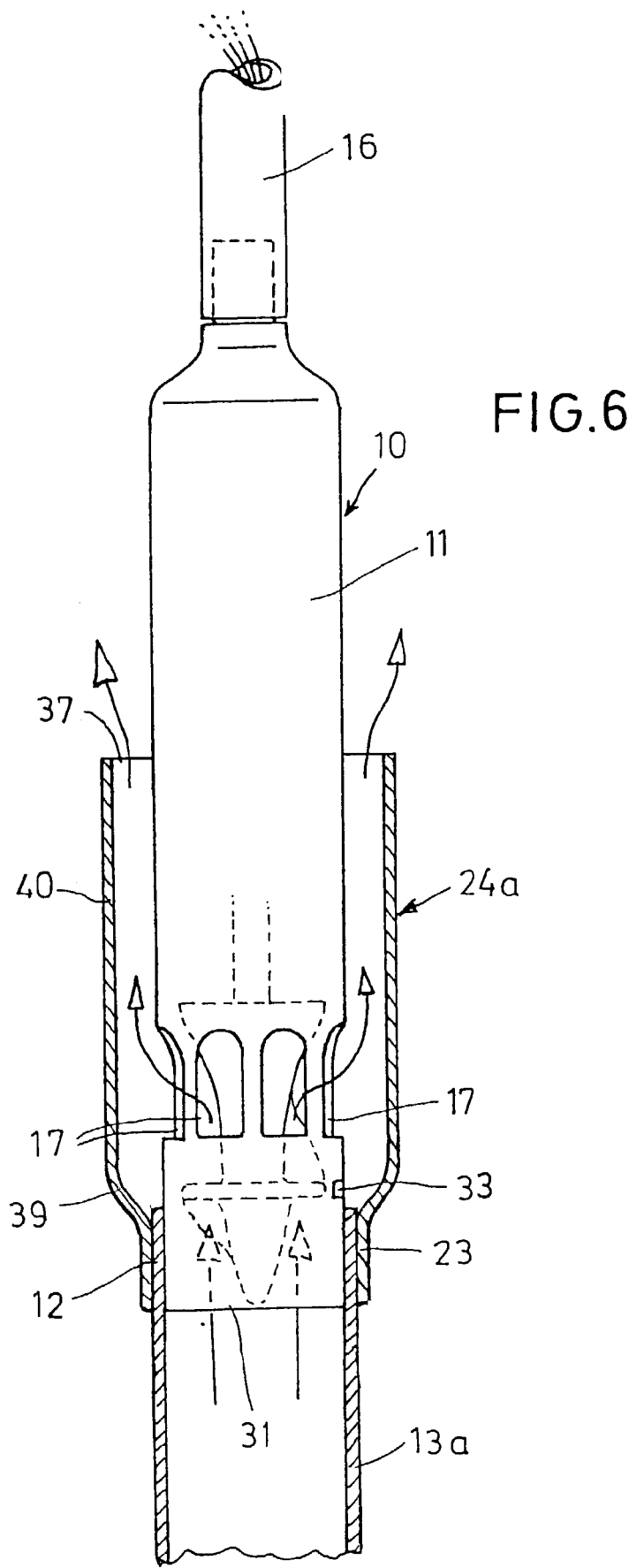

In the Figures:

FIG. 1 is a first embodiment with forward directed delivery direction as an intravascular right ventricular pump operating in a heart, FIG. 2 an enlarged illustration of the blood pump according to FIG. 1, partially broken away, FIG. 3 is a side view of the blood pump according to FIG. 1, FIG. 4 is a sectional view along the line IV—IV of FIG. 3, FIG. 5 is a second embodiment of the blood pump with rearward directed delivery direction when delivering from the right ventricle into the pulmonary artery, and FIG. 6 is an enlarged illustration of the blood pump according to FIG. 5, partially in section.

In FIGS. 1 and 5, a cross-section through a human heart H is shown. The inferior vena cava UHV (vena cava inferior) and the superior vena cava OHV (vena cava superior) open into the right atrium RA. The tricuspid valve TK is located between the right atrium RA and the right ventricle RV. The pulmonary valve PK is located between the right ventricle RV and the pulmonary artery PA. From the pulmonary artery PA, the blood flows via a branching to the left and right lung and from there back to the left atrium LA and the left ventricle LV. The aortic valve AK is located between the left ventricle LV and the aorta AO.

The blood pump 10 is an intravascular blood pump, i.e., an intracardiac blood pump that can be pushed through the blood vessel system of a patient to advance as far as into the heart. The outer diameter is nowhere larger than 10 mm. The blood pump 10 comprises a drive portion 11, a pump portion 12 and a flexible cannula 13 extending from the pump portion 12, at the end of which a discharge opening 14 is located which is spanned by a sail-like tension element. From the rearward end of the drive portion 11, a catheter 16 extends which has a (non-illustrated) lumen for a guide wire and through which electric lines for the power supply of the motor included in the drive portion 11 extend.

Between the drive portion 11 and the pump portion 12, there are flow openings 17 that are admission openings here through which the blood flows into the pump portion 12 to be subsequently pumped through the cannula 13.

The cannula 13 is able to be temporarily extended so that it can be pushed through the superior vena cava OHV. It is biased such that, in the relaxed state, it assumes the U-shaped form illustrated in FIG. 1 wherein it is bent backward from the pump portion, describing a curve of more than 90°, to be positioned, with the discharge opening 14, in the pulmonary artery PA, whereas the flow opening 17 is located in the right atrium RA.

In its construction, the blood pump basically corresponds to that of WO 97/37696 so that its internal structure will not be explained in detail here any more.

In FIGS. 2–4, the basic structure of the blood pump 10 can be seen. The drive portion comprises an elongate cylindrical housing in which the electric motor 19 is located. Via electric lines 20 extending through the catheter 16, the motor 19 is supplied with power from an extracorporeal power source. The lines 20 are connected to a control apparatus regulating the motor 19 such that a desired pump capacity is achieved. On a shaft 21 of the motor 19, a pump wheel 22 is seated which rotates in the pump portion 12 and axially drives the blood. The pump portion comprises a cylindrical pump ring 23 in which the pump wheel 22 is arranged. Between the drive portion and the pump portion 12, there are numerous circumferentially distributed flow openings 17 which, in this embodiment, are inlet openings. The pump ring 23 is adjoined by the cannula 13. The cannula 13 is a flexible hose of polyurethane with an elastic ring reinforcement.

In order to prevent the blood pump from sucking foreign material through the flow openings 17 or from sucking fast on walls, a screen 24 is provided which covers the flow openings 17 at least partially and effects a diversion of the blood stream passing the flow openings. The screen 24 has a cylindrical closed wall 25 covering the flow openings 17 over their entire length, and a front portion with elongate slots 26 as well as a rear portion with elongate slots 27. With its front end 28, the screen 24 is supported on the cannula 13 and the pump ring 23, respectively, and with its inwardly bent rearward end 30, it is supported on the drive portion 11 which it encloses. Under the screen 24, a flow path substantially extends along the entire length of the drive portion 11 so that it is cooled by the blood flowing along. The blood pump of FIGS. 2 and 3 delivers in forward direction, i.e., it sucks through the flow openings 17 and delivers to an end opening 31 at the end of the pump portion 12 or at the transition of the pump portion 12 to the cannula 13. The closed wall 25 of the screen 24 effects the distribution of the suction effect upon the elongate inlet slots 26 and 27 so that local suction peaks are avoided.

A pressure sensor 33 is attached to the pump ring 23. This pressure sensor is a differential pressure sensor detecting the difference between the pressures outside the pump ring 23 and inside the pump ring. Via (non-illustrated) lines, the pressure sensor 33 is connected to the lines extending through the catheter 16. It supplies pressure information to the extracorporeal control apparatus, permitting to detect the momentary capacity of the pump by means of a computer to regulate, e.g., the capacity or delivery rate to a certain value. The sensor 31 also detects a pressure stasis or a local sucking-fast which is then registered as an abnormal operational condition. The sensor 33 is arranged at a distance under the screen 24 so that the screen prevents that foreign matter lays against the sensor from outside. As outer pressure, the sensor 33 always detects the real outer pressure surrounding the pump ring 23. Under the screen 24, the sensor is arranged in the same compartment as the pressure flow opening 17 so that both are subjected to the same pressure. Therefore, sucking or sucking-fast of the pump can be detected by the sensor and used to regulate the capacity of the pump on the basis of the sensor.

The pressure of the pressure sensor 33 cannot only be used to monitor and regulate the pump operation but also to detect the proper positioning of the pump in the heart.

Along the cannula 13, a pressure transmission hose 32 extends that is open at the distal end 34 (FIG. 1). The pressure transmission hose 32 is embedded into the housing of the drive portion 11, and it continues in the catheter 16 (FIG. 2). Its extracorporeal end is connected to a pressure measuring apparatus evaluating the pressure.

The screen 24 surrounds the drive portion 11 and the pump portion 12 at a radial distance of 1 to 2 mm. The screen 24 forms the outer jacket of the blood pump 10. Its outer diameter amounts to about 8 mm and its rigid length amounts to about 40 mm. The screen 24 consists of thin steel where the inlet slots 26,27 are cut out by laser cutting methods.

The embodiment of the blood pump described with reference to FIGS. 3 to 4 reduces the tendency of sucking at the easily deformable material of the right atrium by means of the screen 24 surrounding the flow openings 17. Damage of the tricuspid valve TK and the valvular apparatus with the consequence of the danger of the pump standstill is avoided. The pressure sensor 33 is disposed under the screen 24 in an exposed manner. It cannot be separated from the suction area so that a possible sucking-fast of the blood pump is detected by the sensor as well. According to FIG. 2, the blood stream that radially enters through the inlet slots 26,27 is diverted in axial direction first before it radially passes the flow opening 17.

In FIGS. 5 and 6, an embodiment of the blood pump for delivering from the right ventricle RV into the pulmonary artery PA is illustrated. Here, the blood pump 10 delivers in rearward direction, i.e., towards the catheter 16. In this case, the cannula 13a adjoining the drive portion 11 is straight. At the free end of the cannula 13a, there is the suction opening 35. Through an incision site 36 at or below the branch of the pulmonary artery PA, the pump is introduced into the pulmonary artery. In many cases, the distance of the incision site 36 from the pulmonary valve PK is relatively short. The blood pump 10 should be accommodated completely within the pulmonary artery PA, only the cannula 13a projecting through the pulmonary valve PK. Due to the presence of the screen 24a at the blood pump 10, it is possible to quasi shorten the blood pump, the screen 24a projecting through the pulmonary valve with a portion of the blood pump length and the outlet opening 37 being located about in the middle of the length of the drive portion 11. Thereby, the rigid length of the pump accommodated in the pulmonary artery is considerably shortened.

In FIG. 6, the structure of the blood pump according to FIG. 5 is illustrated in detail. The screen 24a is sealingly seated on the circumference of the pump ring 23 and on the wall of the cannula 13a connected with the pump ring, respectively. The screen 24a has a transition 39 in which it enlarges to the diameter of a cylindrical section 40 extending over the drive portion 11 to about the middle of the length of the drive portion. The cylindrical section 40 ends in an annular outlet opening 37. The blood flows from the cannula 13a through the end opening 31 of the pump ring 23 in which the rotating pump wheel is positioned. Then, the blood flows on through the lateral flow openings into the interior of the closed-wall screen 24a. The screen 24a is open at the axially directed outlet opening 37 only. The blood stream radially exiting from the flow opening 17 is diverted in axial direction by the screen 24*a*. Since the outlet opening is not located at the front end of the blood pump but in the central portion thereof, the operative structural length of the pump is shortened.

Drive portion 11 and pump portion 12 have about the same diameter. The screen 24*a* surrounds the drive portion 11 at a radial distance.

A pressure sensor 33 is provided at the pump ring 23 in the embodiment according to FIG. 6 as well. The pressure sensor 33 is a differential pressure sensor disposed in an opening of the pump ring. The inner sensor surface is exposed to the internal pressure of the pump portion and the outer sensor surface communicates with the interior space of the screen 24*a* and is thus subjected to the outlet pressure of the pump.

Basically, the blood pumps 10 of the two described embodiments have the same structure. They differ from each other in the different delivery directions that can be realized by a corresponding electric control and construction of the pump portion.

The invention claimed is:

1. A blood pump, comprising:
 a drive portion including a motor;
 a pump portion including a pump wheel driven by the motor;
 and at least one lateral flow opening disposed between the drive portion and the pump portion, wherein the flow opening is covered by a screen, configured for diverting a blood flow along the outside of the drive portion prior to entering into or upon exiting from the flow opening.

2. Blood pump according to claim 1, wherein the pump wheel delivers from the flow opening to an end opening of the pump portion and the screen comprises at least one inlet opening at its circumference.

3. Blood pump according to claim 2, wherein the screen comprises at least one inlet opening above the pump portion.

4. Blood pump according to claim 2, characterized in that the screen comprises at least one inlet opening above the drive portion.

5. Blood pump according to claim 1, characterized in that the pump wheel delivers from an end opening of the pump portion to the lateral flow opening and the screen comprises an outlet opening around the drive portion.

6. Blood pump according to claim 5, characterized in that the screen forms a tube that is sealingly connected with the pump portion at one end thereof and the other end of which surrounds the drive portion at a radial distance.

7. Blood pump according to claim 1, characterized in that a pressure sensor is provided at the pump portion, above which the screen rises.

8. Blood pump according to claim 7, characterized in that the flow opening and the pressure sensor under the screen are inseparably coupled to each other in terms of pressure.

9. Blood pump according to claim 1, characterized in that the pump portion is lengthened by a flexible cannula.

10. Blood pump according to claim 9, characterized in that a pressure transmission hose extends along the cannula, which communicates with a catheter connected with the drive portion.

11. Blood pump according to claim 1, characterized in that the screen is mounted exchangeably.

12. Blood pump according to claim 1, wherein said blood pump is configured as an intravascular blood pump, the diameter of the screen being nowhere larger than 10 mm.

* * * * *